United States Patent
Dahlström et al.

(10) Patent No.: US 8,967,145 B2
(45) Date of Patent: Mar. 3, 2015

(54) EXPIRATORY VALVE OF AN ANESTHETIC BREATHING APPARATUS HAVING SAFETY BACKUP

(75) Inventors: Bo Dahlström, Vällingby (SE); Carl Magnus Tornesel, Johanneshov (SE); Lars Danielsen, Hässelby (SE)

(73) Assignee: Maquet Critical Care AB, Solna (SE)

( * ) Notice: Subject to any disclaimer, the term of this patent is extended or adjusted under 35 U.S.C. 154(b) by 1367 days.

(21) Appl. No.: 12/667,544

(22) PCT Filed: Jul. 6, 2007

(86) PCT No.: PCT/EP2007/056880
§ 371 (c)(1),
(2), (4) Date: Jun. 18, 2010

(87) PCT Pub. No.: WO2009/006932
PCT Pub. Date: Jan. 15, 2009

(65) Prior Publication Data
US 2010/0252046 A1     Oct. 7, 2010

(51) Int. Cl.
*A62B 9/02*     (2006.01)
*A61M 16/20*     (2006.01)
*A61M 16/10*     (2006.01)
*A61M 16/01*     (2006.01)
(Continued)

(52) U.S. Cl.
CPC ............. *A61M 16/104* (2013.01); *A61M 16/01* (2013.01); *A61M 16/20* (2013.01); *A61M 16/0081* (2014.02); *A61M 16/205* (2014.02); *A61M 16/206* (2014.02); *A61M 16/209* (2014.02); *A61M 16/0075* (2013.01); *A61M 16/0078* (2013.01); *A61M 16/22* (2013.01); *A61M 2016/0027* (2013.01); *A61M 2205/16* (2013.01)

USPC .................. 128/205.24; 251/129.03; 251/330

(58) Field of Classification Search
USPC ............. 128/201.28, 202.22, 202.27, 203.12, 128/203.13, 203.14, 204.18, 204.21, 128/204.22, 204.29, 205.24, 207.12, 911; 141/18; 251/129.03, 129.14, 129.15, 251/129.17, 330
See application file for complete search history.

(56) References Cited

U.S. PATENT DOCUMENTS 2,630,828 A * 3/1953 Bent .......................... 137/625.64
3,332,445 A * 7/1967 Allen ........................ 137/627.5
3,351,093 A * 11/1967 Frantz ...................... 137/625.27
(Continued)

FOREIGN PATENT DOCUMENTS

DE        29807005 U1 *   7/1998
DE        298 07 005 U1    8/1998
(Continued)

*Primary Examiner* — Justine Yu
*Assistant Examiner* — Christopher Miller
(74) *Attorney, Agent, or Firm* — Steven H. Noll

(57) ABSTRACT

A ventilatory valve controls a pressure level in a patient breathing circuit of an anesthetic breathing apparatus. The ventilatory valve has a valve unit having a controllable restriction to control the pressure level in an expiratory branch of the breathing circuit of the anesthetic breathing apparatus, an electrical operating unit for the valve unit, configured to electrically control the restriction during electrical operation of the anesthetic breathing apparatus, and a non-electrical operating unit (100) for the valve unit, configured to non-electrically control the restriction upon electrical defective or powerless operation of the anesthetic breathing apparatus.

17 Claims, 7 Drawing Sheets

(51) Int. Cl.
*A61M 16/00* (2006.01)
*A61M 16/22* (2006.01)

(56) References Cited

U.S. PATENT DOCUMENTS

| | | | |
|---|---|---|---|
| 3,472,479 A * | 10/1969 | Sherwood | 251/11 |
| 3,768,468 A * | 10/1973 | Cox | 128/204.21 |
| 4,182,599 A * | 1/1980 | Eyrick et al. | 417/328 |
| 4,627,597 A * | 12/1986 | Brausfeld et al. | 251/129.03 |
| 4,898,174 A * | 2/1990 | Fangrow, Jr. | 128/204.24 |
| 4,934,652 A * | 6/1990 | Golden | 251/63.6 |
| 5,237,987 A | 8/1993 | Anderson et al. | |
| 5,542,447 A * | 8/1996 | Foote et al. | 137/113 |
| 5,603,315 A * | 2/1997 | Sasso, Jr. | 128/204.18 |
| 5,875,777 A * | 3/1999 | Eriksson | 128/204.21 |
| 5,950,623 A | 9/1999 | Michell | |
| 5,954,051 A * | 9/1999 | Heinonen et al. | 128/205.24 |
| 5,971,356 A * | 10/1999 | Offenwanger et al. | 251/129.07 |
| 6,000,396 A * | 12/1999 | Melker et al. | 128/204.21 |
| 6,082,705 A * | 7/2000 | Arvidsson | 251/129.07 |
| 6,119,723 A * | 9/2000 | Kenyon | 137/527 |
| 6,186,167 B1 * | 2/2001 | Grumstrup et al. | 137/487.5 |
| 6,959,910 B2 * | 11/2005 | Matsumoto et al. | 251/129.03 |
| 7,604,019 B2 * | 10/2009 | Frampton | 137/81.1 |
| 2002/0017301 A1 * | 2/2002 | Lundin | 128/205.24 |
| 2002/0185127 A1 * | 12/2002 | Melker et al. | 128/202.22 |
| 2003/0084901 A1 * | 5/2003 | Martinez | 128/204.26 |
| 2004/0099267 A1 * | 5/2004 | Ahlmen et al. | 128/203.12 |
| 2004/0144385 A1 * | 7/2004 | Bromster | 128/205.13 |
| 2005/0000570 A1 * | 1/2005 | Mohammed et al. | 137/487.5 |
| 2007/0018127 A1 * | 1/2007 | Seberger | 251/129.04 |
| 2007/0125377 A1 * | 6/2007 | Heinonen et al. | 128/204.21 |
| 2007/0187634 A1 * | 8/2007 | Sneh | 251/30.01 |

FOREIGN PATENT DOCUMENTS

| | | |
|---|---|---|
| EP | 0 911 054 A1 | 4/1999 |
| EP | 1 421 966 A1 | 5/2004 |
| EP | 1 795 222 A1 | 6/2007 |

* cited by examiner

US 8,967,145 B2

EXPIRATORY VALVE OF AN ANESTHETIC BREATHING APPARATUS HAVING SAFETY BACKUP

BACKGROUND OF THE INVENTION

1. Field of the Invention

This invention pertains in general to the field of expiratory valves of an anesthesia patient breathing circuit in an anesthetic breathing apparatus. More particularly, the invention relates to an anesthetic breathing apparatus having an expiratory valve providing control of expiratory flow and pressure during a mechanical ventilation operation mode and providing a pressure-limiting function during manual ventilation operating mode of the anesthesia system.

2. Description of the Prior Art

Anesthesia patient breathing circuits of anesthetic breathing apparatuses, such as anesthesia machines, are utilized to convey gases containing an anesthetic vapor to a patient to carry out a narcosis of the patient. An anesthesia machine having a respiratory anesthesia delivery system comprising such an anesthesia patient breathing circuit provides a mixture of such gases and vaporized anesthetic agents. This mixture is conveyed to the patient via the anesthesia machine's patient breathing circuit.

When patients are subjected to anesthesia, there is usually a transition from spontaneous breathing of the patient, via a phase of manually controlled ventilation when the patient is sedated into anesthesia, to mechanically controlled ventilation, and vice versa when the patient is awakened out of anesthesia. In addition, it is sometimes desired during mechanical ventilation that the operator wants to switch over to a phase of manually controlled ventilation in order to check the condition of the patient, for example in connection with a change in the composition of an anesthetic gas.

Anesthesia patient breathing circuits therefore usually provide manual ventilation as well as automatic mechanical ventilation system, and a ventilation selection switch for selecting between the manual and the mechanical ventilation mode.

In order to limit the maximum pressure during manual ventilation, an adjustable pressure limiting (APL) valve is provided in the anesthesia patient breathing circuit. The APL valve is a pressure relief valve that vents the anesthesia patient breathing circuit when the pressure within the circuit reaches a predetermined level, such that the patient is not subjected to an excessive pressure. The APL valve is adjustable by the user so that differing maximum pressures are allowed in the patient breathing system during an operation and can be determined by the user.

Conventionally, the APL valve is provided with a spring that exerts pressure on a diaphragm that seals off a vent passage against a valve seat. For instance U.S. Pat. No. 5,950,623 discloses such a mechanical APL valve. When the pressure exceeds the spring force, the APL valve opens to vent excess gas into an evacuation system. The valve is adjusted by compressing the spring with a screw mechanism so that the level of the compressed spring force corresponds to the wanted pressure limit.

Such a mechanical APL valve is normally operating independently of any electric power supply to the anesthesia machine. However, the function of such mechanical APL valves may be impaired by a disadvantageously low accuracy of the adjusted pressure limit, as well as an inertial delay during opening.

Furthermore, the mechanical construction of the valve operating unit is subject to wear and tear, which on the one hand limits the life of the operating unit, and which on the other hand leads to an undesired variation of the adjustment mechanism over time. In addition, APL valves of the type disclosed in U.S. Pat. No. 5,950,623 need to be sterilized between patients, e.g. by autoclaving the control knob and valve mechanism. This contributes to an accelerated wear of the APL valve mechanism. Moreover, such mechanical APL valves may be slow in operation. In addition, costs arise for unmounting and disassembling such mechanical APL valves for a necessary cleaning and/or disinfection, e.g. by autoclaving the APL valves, as well as a subsequent re-assembly of the APL valve parts and re-mounting into the anesthesia breathing apparatus.

Hence, APL valves are traditionally components in anesthesia breathing apparatuses, which are cause of a number of issues that need to be eliminated.

An electronic solution for controlling an APL valve is disclosed in EP-A1-1421966 of the same applicant as the present application.

In the unpublished patent application PCT/EP2006/070068 of the same applicant as the present application, which is incorporated herein by reference in its entirety, an electronically controlled APL valve is described. In particular, reference is made to FIG. 1 and FIG. 5 as well as the corresponding description of PCT/EP2006/070068 that illustrates and describes a ventilation system having an electronically controlled APL valve.

However, a drawback of such electronically controlled and operated APL valves is that these do not operate at power failure. These type of APL valves is superior to mechanical APL valves, but they are dependent on an electrical power supply, which may result in a potential safety issue at power failure.

DE29807005U1 discloses an adjustable pressure-relief gas valve that has a valve that is opened by an electromagnetic jack drive and that is pressed closed against a seat, wherein a closure force thereof is adjustable using a bi stable, mechanical, spring based adjustment mechanism. The valve can be moved between operation in an open ventilation position, and a closed position, in which the valve is pressed against a valve seat. The valve is opened by an electromagnetic jack drive with a connecting rod to adjust the operation position of the valve. The valve is intended for use with an anesthetic-control unit or a patient respiration unit, in order to change the operation mode of the unit between manually controlled and spontaneous patient respiration. The valve setting can be selected from a central control unit and displayed on a monitor. A manual function remains available for emergencies, e.g. power failures, facilitating change to manual operation. However, the valve has to be switched manually by means of a lever to the emergency mode and in this emergency mode the valve functions as a conventional mechanical, spring biased, pressure limiting valve with all the drawbacks thereof.

Thus, there is a need for an electronically controlled APL valve, which during power failure situations may be operated independently of an electrical power supply with a similarly advantageous mode of operation as an electronically controlled APL valve.

Hence, an improved electronically controlled valve providing an adjustable pressure limit, which during power failure situations may operate independently of an electrical power supply, would be advantageous. In particular such an electronically controlled valve allowing for increased patient safety by providing the possibility to both work electronically with high precision and which operates independently of a power supply at power failure situations, and which is sufficiently sensitive and fast in operation as an electrically controlled valve, would be advantageous.

SUMMARY OF THE INVENTION

Accordingly, embodiments of the present invention seek to mitigate, alleviate or eliminate one or more deficiencies, disadvantages or issues in the prior art, such as the above-identified, singly or in any combination, by providing a ventilatory valve, an anesthetic breathing apparatus, and a method.

According to a first aspect of the invention, an expiratory ventilatory valve is devised to control at least one of a expiratory flow or an expiratory pressure level in an expiratory branch of a patient breathing circuit of an anesthetic breathing apparatus. The ventilatory valve has a valve unit having a controllable restriction to control the expiratory flow and/or expiratory pressure in the breathing circuit, an electrical operating unit for the valve unit, configured to electrically control the restriction during electrical operation of the anesthetic breathing apparatus, and a non-electrical operating unit for the valve unit, configured to non-electrically control the restriction upon electrical defective or powerless operation of the anesthetic breathing apparatus.

According to a second aspect of the invention, an anesthetic breathing apparatus has a ventilatory valve according to the first aspect of the invention. The anesthetic breathing apparatus has a manually operable emergency manual ventilation switch, which normally is in an off-position in which the anesthetic breathing apparatus in normal operation is supplied with electrical power and operational for at least one electrically controlled mechanical ventilation mode and a manual ventilation mode, and wherein, when the emergency manual ventilation switch is an on-position, the anesthetic breathing apparatus is disconnected from the electrical power and operational in a pneumatically controlled manual ventilation operation mode; whereby the ventilatory valve during the normal operation is electrically controlled and in the pneumatically controlled manual ventilation operation mode is non-electrically controlled.

According to a third aspect of the invention, a method for controlling a pressure level in a breathing circuit of an anesthetic breathing apparatus according to the second aspect of the invention, by means of a ventilatory valve according to the first aspect of the invention, is provided. The method includes electrically controlling a controllable restriction of the ventilatory valve during electrical non-faulty operation of the anesthetic breathing apparatus, and upon electrical faulty operation or upon emergency operation of the anesthetic breathing apparatus non-electrically controlling the controllable restriction of the ventilatory valve.

Some embodiments of the invention provide for a more accurate and flexible control of an adjustable pressure limiting (APL) function during electrically faulty operation, power failures, and/or emergency operation of an anesthetic breathing apparatus.

Some embodiments of the invention also provide for a substantially maintenance free expiratory valve operating unit arranged for regulating PEEP during mechanical ventilation and providing an adjustable pressure limit during manual ventilation both during normal and emergency operation. Some embodiments of the invention provide for a long service life of the expiratory valve operating unit without the need of servicing the unit or replacing wearing parts thereof.

DESCRIPTION OF THE PREFERRED EMBODIMENTS

Figure 1:
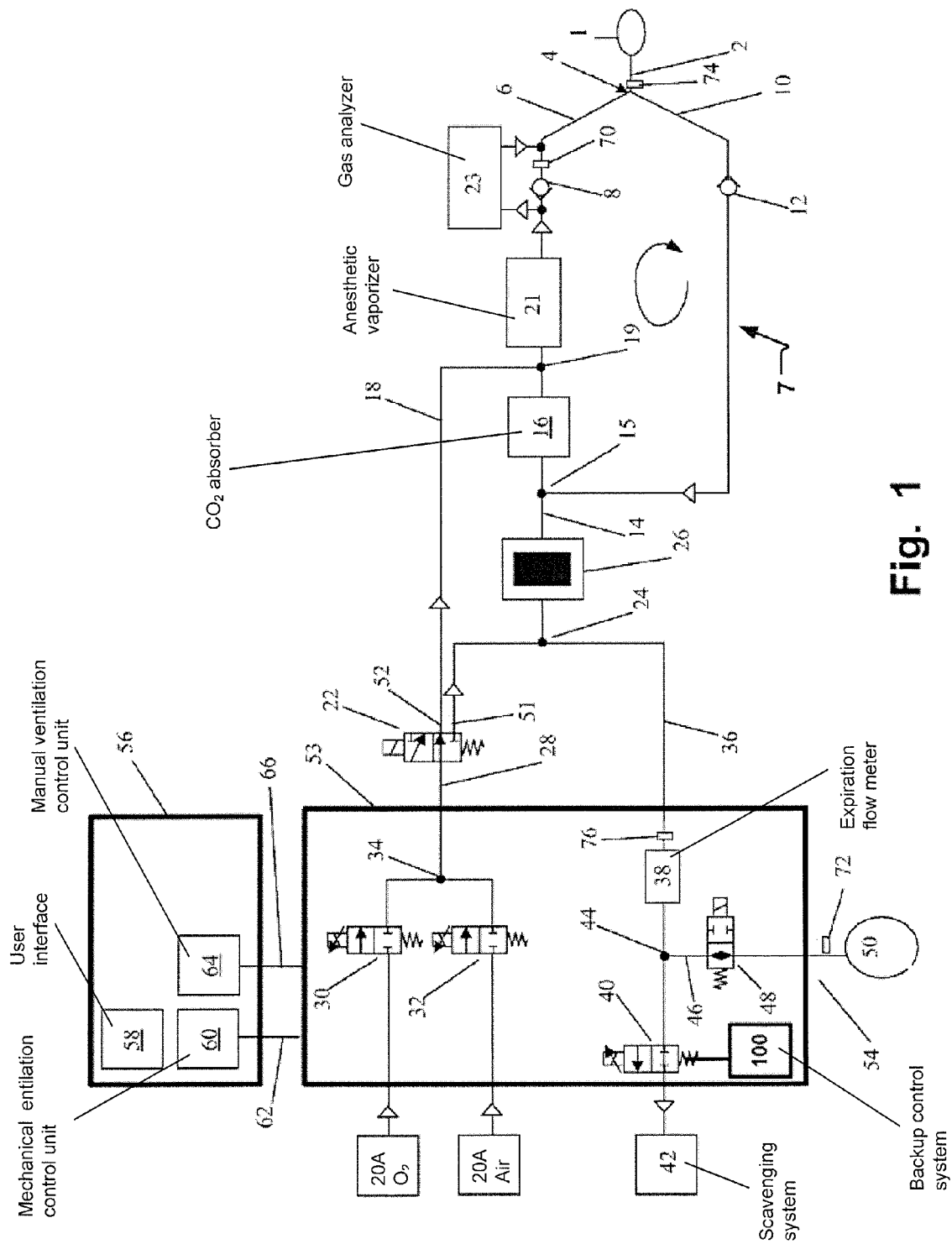
FIG. 1 is a schematic drawing of an anesthetic breathing apparatus comprising an embodiment of an expiratory valve with non-electrical valve backup.

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIG. 1 shows schematically, a breathing circuit of an anesthetic breathing circuit, coupled to a circle system 7 with a mechanical ventilation system 53 and a manual ventilation system 54.

The airways of a patient 1 are connected to a patient tube 2 of a Y-piece 4 in a circular tubing system with an inspiration tube 6 provided with a one-way inspiratory valve 8 and an expiration tube 10 provided with a one-way expiratory valve 12. A patient pressure sensor 74 is provided in the patient tube 2 connected to the Y-piece 4. Downstream the one-way expiratory valve 12, in FIG. 1 in a clockwise direction along the circle system, a common expiration and inspiration line 14 is provided for the delivery of inspiration gas to the patient and evacuation of expiration gas from the patient. The common expiration and inspiration line 14 is coupled to the circle system 7 at a junction 15. Further along the circle system 7, the tubing passes through a $CO_2$ absorber 16 and downstream the $CO_2$ absorber 16 a fresh gas supply branch line 18 is provided to feed fresh inhalation gas into the circle system 7 from a fresh inhalation gas source. The fresh gas supply branch line 18 is coupled to the circle system 7 at a junction 19. The fresh gas inhalation source may comprise multiple gas sources, such as an oxygen gas source 20A and an air gas source 20B, as illustrated in FIG. 1. Downstream the junction 19, an anesthetic vaporizer 21 is arranged, which is devised for vaporizing a volatile anesthetic agent in the flow of inspiration gas to the patient 1. In an exemplifying breathing circuit the vaporizer 21 may be an injection type vaporizer in order to work properly with the mechanical ventilation system 53 as well as with the manual ventilation system 54. A gas analyzer 23 is provided to analyze gas contents with an input of sample inspiratory gas in a sidestream. The sidestream is tapped downstream of the anesthetic vaporizer 21 and upstream of the one-way inspiratory valve 8. After analysis in gas analyzer 23, the sample gas is recirculated to the inspiratory flow downstream of the one-way inspiratory valve 8 and upstream of the Y-piece 4. A pressure sensor 70 is provided between the one-way inspiratory valve 8 and the recirculation point of the sample gas.

The common expiration and inspiration line 14 may be provided with an adsorption filter 26 devised for adsorption and desorption of anesthetic and respiration gases to or from the patient.

At the side turned opposite the circle system 7, the adsorption filter 26 of the common expiration and inspiration line 14, is coupled at a junction 24 to a first output branch line 51 from a selection valve 22, here in the form of a bypass valve. A second output branch 52 of the selection valve 22 is coupled to the fresh gas supply line 18. At an input side, the selection valve 22 is coupled to an input line 28 connected to the fresh inhalation gas source. The selection valve 22 is devised to select the flow route for the fresh inhalation gas via the supply branch line 18 or via the common expiration and inspiration line 14 downstream the adsorption filter 26 into the circle system 7.

Oxygen gas source 20A is coupled to an O2 inspiratory valve 30 that in its turn is connected to the selection valve input line 28 at a blender 34. Similarly, air gas source 20B is coupled to an air inspiratory valve 32 that also is coupled to the selection valve input line 28 at the blender 34. The O2 inspiratory valve 30 and the air inspiratory valve 32 are devised for adjusting the inlet flow and the proportions of the respective gases into the input line 28. Only O2 and air are shown, but nitrous oxide may also be used as is common in the art.

In FIG. 1 the selection valve is a bypass valve 22 which has the function of selecting fresh inhalation gas flow either through the first output branch 51 or through the second output branch 52 of the selection valve 22. Thus, with the selection valve being actuated to a first flow selection mode the fresh inhalation gas is enabled to flow to the patient via the common expiration and inspiration line 14 and through the adsorption filter 26, or via the supply branch line 18 then bypassing the adsorption filter 26 as well as the CO2 absorber 16.

An evacuation line 36 is connected to the common expiration and inspiration line 14 and to the mentioned first output branch line 52 at the is junction 24. The evacuation line 36 leads via a flow meter 38 and a pressure sensor 76 to an expiratory valve 40 that is devised to control output of evacuated gas flow from the circle system 7 to a scavenging system 42 or to the atmosphere. A manual ventilation line 46 is connected to the evacuation line 36 at a junction 44. The manual ventilation line 46 is provided with a manual ventilation valve 48 and leads to a manual bag 50 devised for manual ventilation. In one embodiment there is a pressure sensor 72 provided on the manual bag side of the manual ventilation valve 48.

The mechanical ventilation system 53 and the expiratory valve 40 as well as other components may be parts of a known mechanical ventilator with a ventilation control system 56. The ventilation control system 56 may comprise a user input/output interface 58 with command input means and display means of a known type. The interface may also be provided with remote control means for remote control of the manual expiratory valve functions or characteristics. The remote control function may for example be realized in a known manner as shown in EP1426966, where an anesthetic machine is provided with remote control for controlling alarms and transitions between mechanical ventilation and manual ventilation.

Also in a known manner, the ventilation control system 56 may have a mechanical ventilation control unit 60 usually including specifically designed computer program code for controlling the operation of the mechanical ventilation system 53 and its components via a symbolically shown control line 62. The mechanical ventilation control unit 60 enables vent of breathing gas from the mechanical ventilation system according to a first set of predetermined control rules for controlling the expiratory valve 40 in accordance with mechanical ventilation mode requirements. In effect, the expiratory valve may in this connection be controlled to open or close at predefined pressure levels that occur in the tubing system. For instance, the control rules implement pressure control functions of the patient pressure. During expiration, a positive end expiratory pressure (PEEP) may be adjusted by the expiratory valve 40 at the end of the expiratory breathing phase, before the next inspiration phase starts. The expiratory valve 40 is usually closed during inspiration and controls the expiratory pressure level, and expiratory flow, during expiration.

The ventilation control system 56 further comprises a manual ventilation control unit 64. The a manual ventilation control unit 64 is devised to control the expiratory valve 40 via the symbolically shown control line 66 according to a second set of predetermined control rules and enable mechanical ventilation features adapted to manual ventilation mode requirements.

In the manual ventilation mode, the manual ventilation valve 48 is actuated to an open position in order to allow gas flow in the manual ventilation line 46 to and from the manual ventilation bag 50, and the manual ventilation control unit 64 is activated to control the expiratory valve 40. The effect of this is that the same expiratory valve 40 is used for the manual ventilation system as well as for the mechanical ventilation system, but is controlled according to different sets of control rules. Switching over from mechanical to manual ventilation mode, and vice versa, involves actuating the manual ventilation valve 48 to enable the selected ventilation mode as well as selecting the corresponding ventilation control mode on the user input/output interface 58 of the ventilation control system 56. When the manual ventilation control mode is selected on the ventilation control system 56, the mechanical ventilation mode functions for the expiratory valve 40 are disabled.

The manual ventilation control mode is in different embodiments adapted to different manual ventilation mode requirements. For this purpose the manual ventilation control unit 64 includes different subsets of predetermined manual ventilation control rules.

Hence, the expiratory valve 40 is operational as conventional expiratory valve during mechanical ventilation and as an APL valve during manual ventilation. The expiratory valve 40 is operational to limit the maximum pressure during manual ventilation, in accordance with an electronically controlled adjustable pressure limiting (APL) valve. Hence, expiratory valve 40 implements both a conventional expiratory valve and an APL valve. When functionally operated as an APL valve during manual ventilation, the expiratory valve 40 implements an electronically controlled pressure relief valve for venting the anesthesia patient breathing circuit when the pressure within the circuit reaches a predetermined level, such that the patient is not subjected to an excessive pressure. Operation of the APL valve function is made with high precision. The opening pressure of the expiratory valve 40 is electronically adjustable by the user so that differing maximum pressures are allowed in the patient breathing system during an operation and can be determined by the user.

In addition, the expiratory valve 40 is implemented with a non-electrical expiratory valve backup control system 100. The non-electrical expiratory valve backup control system 100 may be brought into operation during power failures when the electrical control system for the expiratory valve 40 is not operational. The non-electrical expiratory valve backup control system 100 may also brought into operation upon other defects in the anesthetic breathing apparatus. For instance, it may occur that an anesthetic breathing apparatus locks itself in operation, e.g. due to a component defect, or operating error thereof. Further, the non-electrical expiratory valve backup control system 100 provides for a security backup function, e.g. during power failures or other emergency situations. Moreover, the non-electrical expiratory valve backup control system 100 may be brought manually into operation or may be automatically brought into operation during power failures, detected defects, or emergency situations. The non-electrical expiratory valve backup control system 100 enables a function of the expiratory valve 40 during such power failure, or other electrical failure situations, which is similar to the electrically controlled operation. Emergency or backup operation of the expiratory valve 40 is independent of electrical power. This means that the expiratory valve 40 may provide an APL valve function with high precision, even during such electrical failure situations. Embodiments of the non-electrical expiratory valve backup control system is described in more detail below, with reference to FIGS. 5, 6, 7 and 8.

Figure 2:
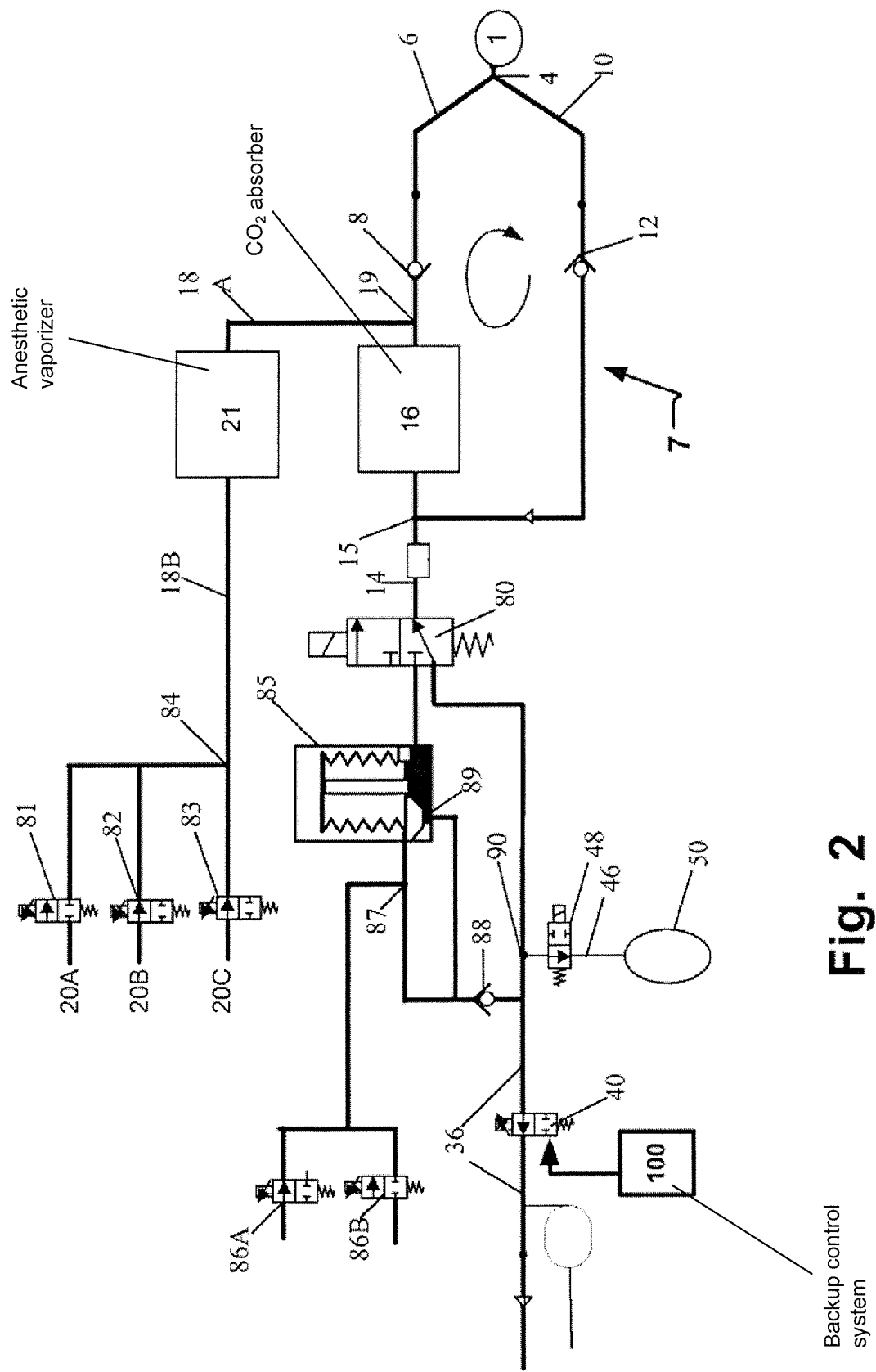
FIG. 2 is a schematic drawing of another anesthetic breathing apparatus comprising an embodiment of an expiratory valve with non-electrical valve backup.

Similarly, the configuration of another anesthetic breathing apparatus, shown in FIG. 2, includes a common expiratory valve 40 for manual and mechanical ventilation in an evacuating line 36, as well as a fresh gas inhalation source comprising an oxygen gas source 20A and an air gas source 20B. The embodiment shown in FIG. 2 additional comprises a nitrous oxide gas source 20C. The fresh gases from sources 20A, 20B, and 20C enter the fresh gas supply line 18B after passing through valves 81, 81, and 83 and junction 84. Unlike the embodiment shown in FIG. 1, the anesthetic agent vaporizer shown in FIG. 2 is not in the circle system 7 but is connected to the circle system 7 at junction 19 through fresh gas supply line 18A. The expiratory valve 40 shown in FIG. 2 is also provided with a non-electrical expiratory valve backup control system 100. This expiratory valve 40 is used to control the pressure level in the expiration branch, including expiratory tube 10, and the inspiration branch, including inspiratory tube 6, of the patient circle system 7. The same expiratory valve 40 is used by the manual ventilation as well as by the mechanical ventilation system, but is controlled according to different first and second sets of control rules. During power failure or other emergency situations, the expiratory valve 40 may be operated non-electrically by means of the electrical expiratory valve backup control system 100.

The implementation of FIG. 2 includes a "bag in bottle" 85 to drive the breathing gas in the circle system 7. This bag in bottle 85 is provided with a, so called, pop-off valve 89, releasing excess gas from the breathing circuit to an evacuation system. In FIG. 2 the driving gas in the mechanical ventilation system is provided to the outside, side of the bag in bottle 85. The expiratory valve 40 controls the pressure of the driving gas by regulating a restriction in the evacuating line 36. Thereby the flow of the driving gas through the expiratory valve 40 to evacuation (EVAC) is regulated, and the pressure in the breathing circle is controlled by the pressure of the drive gas by means of the bag in bottle 85. Gas sources (O2 and air) are connected via supply valves 86A, 86B, respectively, and further to a junction 87 connecting the gas sources to the bag in bottle 85 and the expiratory valve 40 via a one-way valve 88 and a junction 87. In this way the O2 and air sources provide driving gas, during mechanical ventilation, to the bag driving the breathing gas inside the bag and which driving gas pressure is adjusted by, means of controlling, the expiratory valve 40. The manual ventilation bag 50 is connected to the evacuation line 36, including the expiratory valve 40, via the junction 90.

Between the bag and the junction 90 is provided a manual ventilation valve 48 for selecting manual ventilation. The junction 90 connects the manual ventilation bag 50 to the expiration branch 36 with the expiratory valve 40 and to the breathing circle via a selection valve 80 and the common inspiration and expiration line 14. Thus, the expiratory valve 40 controls the pressure provided by the manual bag 50 to the breathing gas flow in the circle system 7. The selection valve 80 arranged in the common inspiration and expiration line 14 selectively connects the bag in the bag in bottle 85 and the manual ventilation bag 50 to the breathing gas circle. Thus, the manual ventilation system, driven by the manual bag, is connected to the breathing circle providing gas flow to and from the circle and excess gas through expiratory valve 40 controlling the pressure by controlling the flow of breathing gas, or supplied fresh gas to the breathing circuit.

The control rules are different in the mechanical mode and in the manual mode, though, the expiratory valve is identical. The breathing apparatuses in FIG. 1 and FIG. 2 adjust the pressure level in the circle system 7 according to these rules, by controlling the electronic expiratory valve 40. FIG. 1 illustrates control means 60, 64 in the control system 56 that controls the expiratory valve 40.

The apparatus in FIG. 2 may in addition include control means, for example including a control unit such as a computer, to adjust the expiratory valve, (not shown in the FIGS.). Moreover, the ventilator in FIG. 2 includes a ventilation control system including components for controlling mechanical and manual ventilation and a user input/output interface with command input means and display means of a known type. The ventilation control system comprises computer program code for controlling the operation of the mechanical ventilation and manual ventilation, which enables the electronic expiratory valve 40 to open or close at pre-defined pressure levels and thereby limit the pressure in the breathing circuit, according to a first set of predetermined control rules during mechanical ventilation mode, controlling pressure such as a PEEP valve function, and according to a second set of predetermined control rules during manual ventilation enabling and adapting mechanical ventilation features for manual ventilation mode requirements.

The configuration includes the manual ventilation valve 48, the opening of which allows gas to flow to the manual ventilation bag 50 via line 46 and activates the manual ventilation mode and, thus, activating the control of the electronic expiratory valve 40 in accordance with the second set of rules adapted for manual ventilation requirements. As in FIG. 1, the same expiratory valve 40 is used for the manual ventilation system, as well as for the mechanical ventilation system, but is controlled according to different sets of control rules. Switching over from mechanical to manual ventilation mode, and vice versa, involves actuating the manual ventilation valve 48 to enable the selected ventilation mode as well as selecting the corresponding ventilation control mode on the user input/output interface of the ventilation control system. When the manual ventilation control mode is selected on the ventilation control system, the mechanical ventilation mode functions for the expiratory valve 40 are disabled.

The mechanical ventilation system, comprising driving means, i.e. gas supply selection valves 30, 32 (FIG. 1), 86A, 86B (FIG. 2), and the expiratory valve 40 controls the mechanical ventilation. The manual system, including the manual bag 50, as driving means, and the expiratory valve 40 is used to control the manual ventilation.

In accordance with FIG. 1 the pressure level in the breathing circuit are controlled by controlling the flow of breathing gas through expiratory valve 40 during both mechanical and manual ventilation.

In accordance with FIG. 2, the pressure level in the breathing circuit is controlled by controlling the flow of breathing gas through expiratory valve 40 during manual ventilation, and by controlling the flow of driving gas through expiratory valve 40 during mechanical ventilation.

Figure 3:
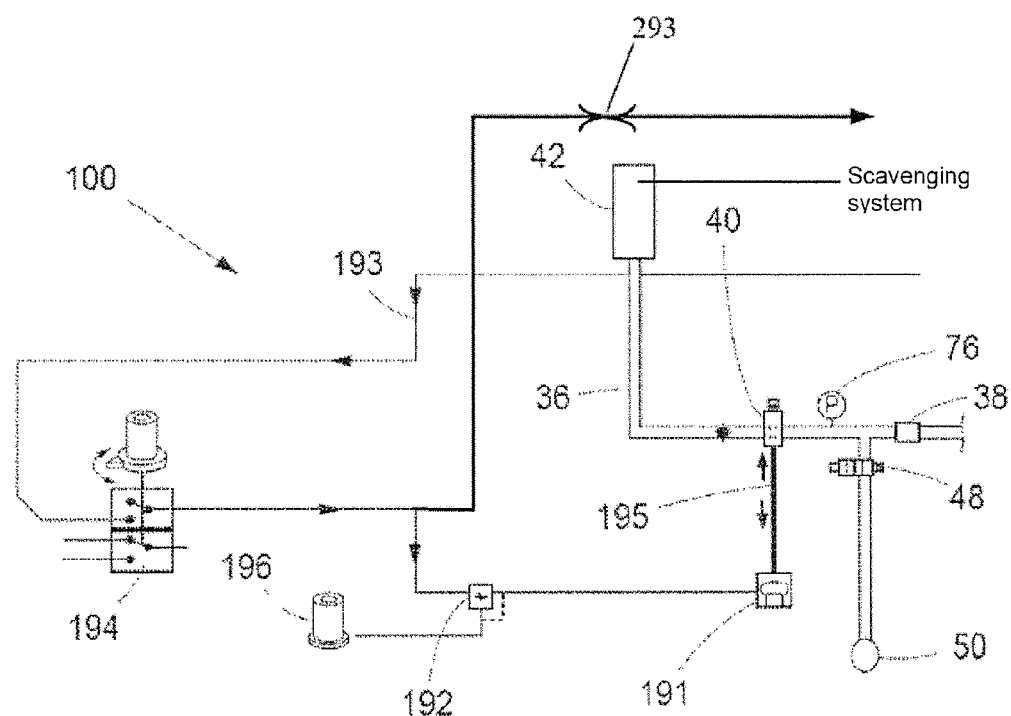
FIG. 3 is a detailed scheme of a expiratory portion of a further anesthetic breathing apparatus with an expiratory valve according to an embodiment with non-electrical valve backup.

A detailed pneumatic schematic drawing of an embodiment of an expiratory portion of a further anesthesia machine including the expiratory valve 40 is shown in FIG. 3.

An expiration branch from a patient extends to an expiration flow meter 38 and an expiration pressure meter 76. A manual ventilation bag 50 is provided for manual ventilation by a user.

Downstream the expiration pressure meter 76, the expiration path extends to a scavenging system 42.

An expiratory valve 40 is arranged in the evacuation line 36 for controlling the pressure and flow in the line, as elucidated above. If the pressure during manual ventilation exceeds a predetermined pressure value, the valve is opened and relieves the pressure in a precise and controlled manner. The expiratory valve 40 is normally controlled via an electric control circuit based on the pressure meter 76 and other signals. During mechanical ventilation, a PEEP may be maintained by means of the expiratory valve 40.

In the embodiment shown in FIG. 3, the expiratory valve 40 is in addition backed up for control by a pneumatic circuit comprising a mushroom valve assembly 191. The mushroom valve assembly 191 is provided with control gas under pressure from an adjustable pressure regulator 192. The pressure regulator 192 is for instance provided with pressurized oxygen or pressurized air via a line 193. The adjustable pressure regulator 192 may for instance be mechanically controlled by a knob 196.

Line 193 also comprises a manually operable emergency manual ventilation switch 194, which normally is in an off-position. Emergency manual ventilation switch 194 is a combined electrical switch and a pneumatic switch, in which the pneumatic line 193 is interrupted and in which electric power supply to the anesthesia machine is controllable. The emergency manual ventilation switch 194 may be provided in the operating panel of the anesthesia machine. The emergency manual ventilation switch 194 may be provided as a separate switch overriding an existing power on/off switch. For safety reasons the emergency manual ventilation switch 194 may be arranged inside a housing or cover that has to be removed before access to the emergency manual ventilation switch 194. Thus, activation by mistake of the emergency manual ventilation switch 194 is precluded.

The emergency manual ventilation switch 194 may alternatively be automatically electrically operated so that it enters its emergency position as soon as a power failure is present. The emergency manual ventilation switch 194 may then be required to be manually moved back to the normal position so that normal operation is not re-entered without being requested by the operator. Alternatively, normal operation may be resumed after a predetermined time period after the return of the electric power, for example one minute.

Figure 4:
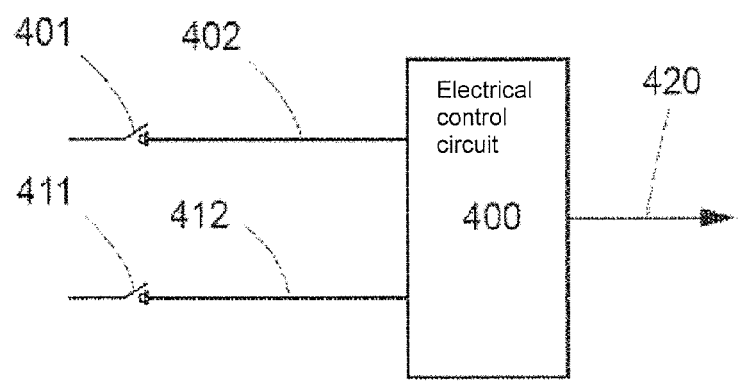
FIG. 4 is a schematic illustration of a control circuit for an emergency ventilation mode of an anesthetic breathing apparatus.

FIG. 4 is a schematic illustration of an electrical control circuit 400 for an emergency ventilation mode of an anesthetic breathing apparatus. The electrical switch part 411 of the emergency manual ventilation switch 194 inputs the on or off condition for the emergency manual ventilation mode to the control circuit 400 via a line 412. A conventional power on/off switch 401 electrically controls a line 402 that is input into the control circuit 400. The control circuit 400 includes suitable logic units for controlling an output line 420 that controls the electrical power supply to an anesthetic breathing apparatus. Output line 420 is chosen to shut off the power supply when either the power off switch is put into an "off" position and/or when the emergency manual ventilation switch 194 is put into an "on" position. That means the emergency manual ventilation switch 194 electrically overrides the conventional power on/off switch of the anesthesia breathing apparatus' power supply.

In addition, the emergency manual ventilation switch 194 includes a pneumatic switch, as mentioned above. When the emergency manual ventilation switch 194 is put into the "on" position, the pneumatic line 193 is released for gas supply to the pressure regulator 192. At the same time, gas supply to the patient circle is provided via a flow regulator 293. That means that at the same time as electrical power is shut off, a metered amount of oxygen or air may be supplied to the patient 1, controlled by manual ventilation bag 50. This flow may be adjustable by flow regulator 293 to a desired flow rate sufficient for ventilating a patient, such as between 0.1 to 15 liter/minute, such as 7 liter/minute. This flow provides that the pressure regulator 192 is pressurized.

The output pressure of the pressure regulator 192 may be controlled by a suitable wheel or knob, e.g. on the operating panel of the anesthesia breathing apparatus, for instance denominated "Emergency Ventilation APL".

The same wheel or knob that under normal operating conditions is used for adjusting the APL function may be used for the adjustment of the emergency pressure regulator 192.

The output pressure from pressure regulator 192 is conveyed to a compression cylinder, pressure cylinder, or a similar pressure conversion unit that is capable of converting the adjusted pressure to a mechanical movement. The pressure conversion unit may be implemented in form of a mushroom valve assembly 191, which comprises a mushroom membrane that expands when pressurized, and thus may transfer the motion of the mushroom membrane to a driving axle, push rod, or similar force transmission unit 195 that is moved in relation to the pressure in a pressurized mushroom cavity of the mushroom valve assembly 191. Alternatively to a mushroom a valve, a pressure cylinder may be employed.

The force transmission unit 195 is connected to the actuator that in normal operation under electrical control controls the APL pressure, i.e. in the illustrated embodiments the expiratory valve 40.

Alternatively, the force transmission unit 195 may directly or indirectly affect a specific, separate membrane, which is mounted in the same channel as the membrane for the normal operation APL function. In this case, the pressure from pressure regulator 192 may directly, or via the force transmission unit, control the pressure in this channel via this separate membrane. However, such a solution with an electrical valve unit that is active when a power supply is available, and a separate backup valve unit that is operative upon power failure or similar emergency ventilation modes, comprises two expiratory valve membranes. The two membrane systems are either arranged in series or in parallel and thus the cost is increased compared to one membrane systems. Furthermore cleaning or disinfection of two membrane systems is inferior compared to one membrane systems. Therefore embodiments comprising integrated electrical valve units and non-electrical valve units are even more advantageous than systems where these two units are arranged separately.

The emergency manual ventilation switch 194 may alternatively be automatically electrically operated so that it enters its emergency position as soon as a power failure is present. The emergency manual ventilation switch 194 may then required to be manually moved back to the normal position so that normal operation is not re-entered without being requested by the operator. Alternatively, normal operation may be resumed after a predetermined time period after the return of the electric power, for example one minute.

Figure 5:
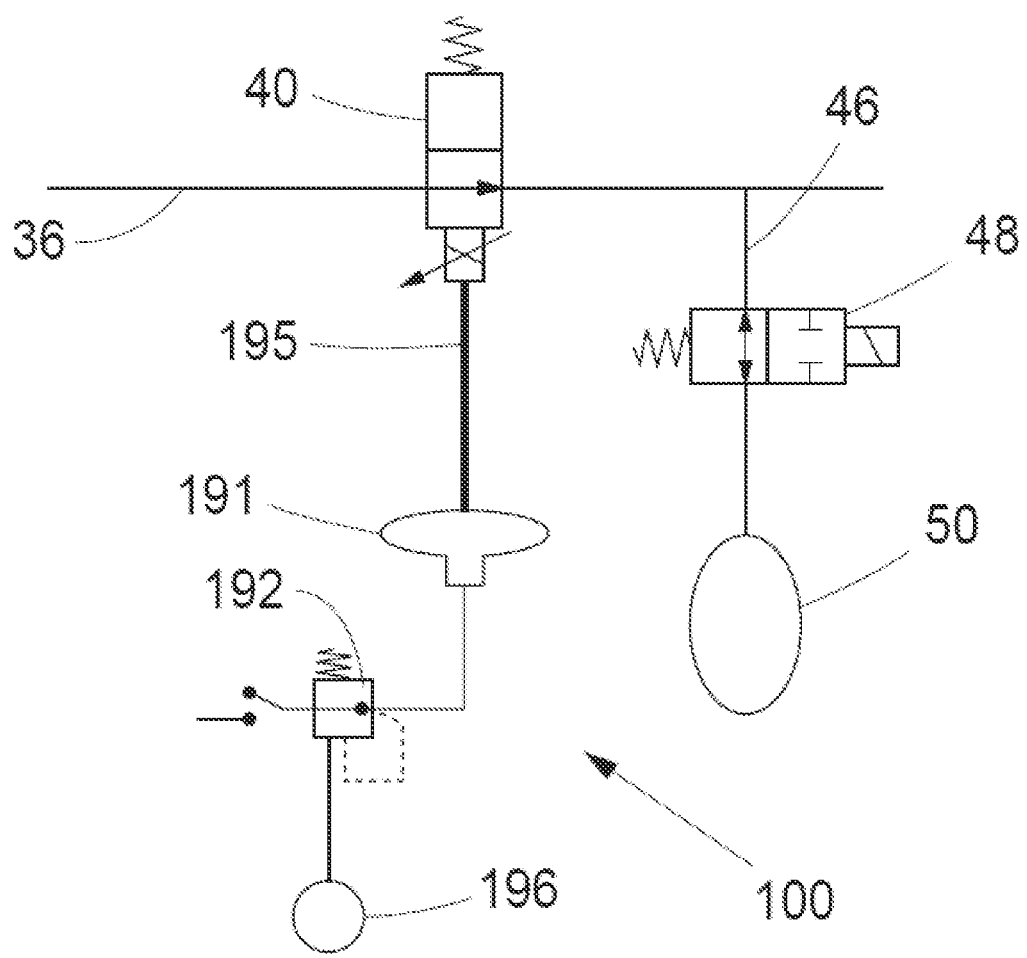
FIG. 5 is a schematic detailed view of the embodiment of the expiratory valve of FIG. 3.

The mushroom valve assembly 191 of FIG. 3 is shown in further detail in FIG. 5 and comprises a mushroom membrane, which is expanded when the pressure inside the mushroom valve assembly 191 increases. The expansion operates on force transmission unit 195 in the form of a push rod, which exerts a pressure on the expiratory valve 40, e.g. a membrane thereof. The force thus provided has a defined relation to the pressure inside the mushroom valve, for instance it is proportional to the latter. Thus, the operating pressure of the expiratory valve 40 may be controlled by the pressure provided to the mushroom valve assembly 191, which in turn is controlled by the adjustable pressure regulator 192.

The adjustable pressure regulator 192 may be adjusted by a manual knob 196, which may be separate or may be comprised in the same knob as the electric adjustment knob for the electric operation of the expiratory valve 40, which is used by the operator during mechanical ventilation. The gas provided to the adjustable pressure regulator 192 may be any gas under a pressure, which is sufficient for operating the push rod 195. Since both pressurized air or nitrous oxide, and oxygen are present, any of these sources may be used by suitable pneumatic arrangements of gas sources thereof.

In normal operation the pneumatic backup system comprising the mushroom valve assembly 191 is completely disconnected from the expiratory valve 40. The backup operation is not initiated until an emergency mode is activated by means of emergency manual ventilation switch 194.

Figure 6:
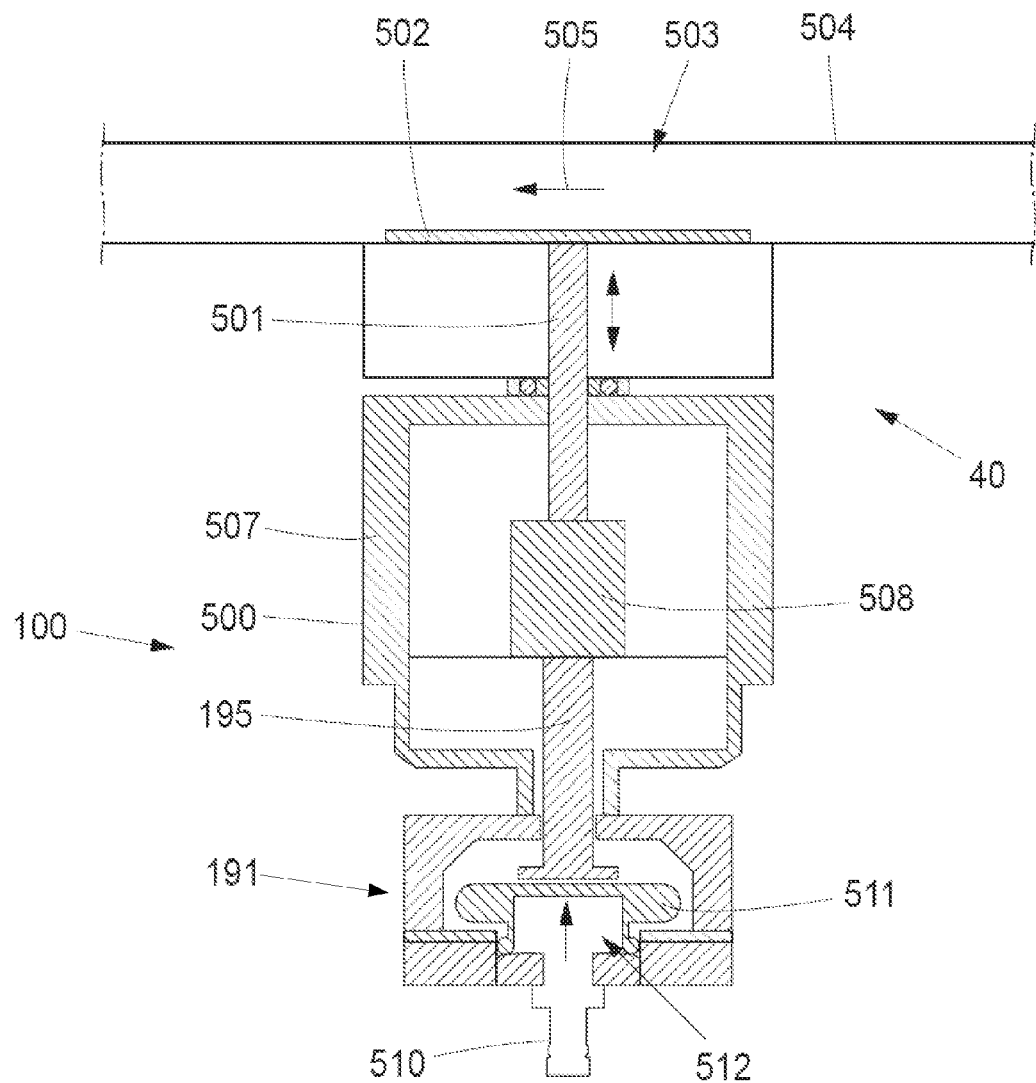
FIG. 6 is a cross-sectional view of an expiratory valve according to an embodiment.

FIG. 6 is a cross-section of a practical implementation of the embodiment of FIG. 5. The normally electrically operated expiratory valve 40 comprises a non-electrical expiratory valve backup control system 100. The expiratory valve 40 comprises a solenoid 500 driving a push rod 501 connected to an expiratory valve membrane 502. The solenoid comprises for instance a permanent magnet 507 and a coil 508. An electrical current in coil 508 thus causes a relative movement of the coil and the push rod 501 in a longitudinal direction of the latter.

The expiratory valve membrane 502, when actuated upon by the push rod 501, changes a restriction 503 in an expiratory gas flow channel 504. Thus, an expiratory gas flow 505 and a pressure level in the expiratory gas flow channel 504 is controlled by the position of expiratory valve membrane 502 therein. In electrical operation of the anesthesia breathing apparatus, in which the expiratory valve 40 is installed, the solenoid is operated electrically in order to control the restriction 503.

During emergency manual ventilation the non-electrical expiratory valve backup control system 100 takes over control of restriction 503. The force transmission unit 195 in form of a push rod is controlled by the mushroom valve assembly 191. In more detail, the mushroom valve membrane 511 is expanded when the pressure in the interior 512 of the mushroom valve increases. The expansion is controlled pneumatically via an input 510, and operates on force transmission unit 195, which exerts a pressure on the expiratory valve membrane 502 via the push rod 501 of the inactive solenoid 500. Force transmission is provided by engagement of the force transmission unit 195 with the push rod 501, perhaps via a suitable abutment in the interior of the solenoid 500. The force thus provided has a defined relation to the pressure inside the mushroom valve assembly 191, as explained above. Thus, the operating pressure of the expiratory valve 40 may be non-electrically controlled by the pressure provided to the mushroom valve assembly 191, which in turn for instance is controlled by the adjustable pressure regulator 192, shown in FIG. 3 and FIG. 5.

Figure 7:
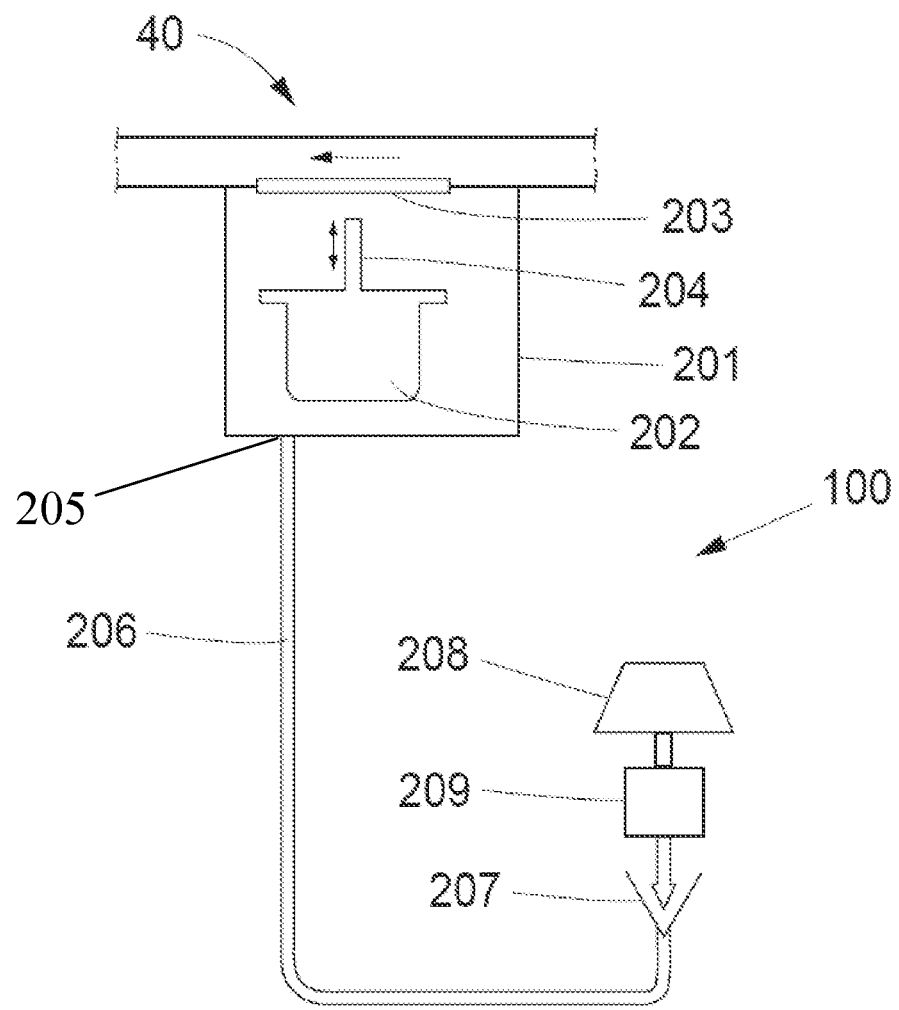
FIG. 7 is a schematic view of another embodiment of an expiratory valve.

Another embodiment of the expiratory valve 40 having non-electrical backup operation is shown in FIG. 7. The expiratory valve 40 is provided with a sealed housing providing a sealed chamber 201 in which an electric solenoid 202 is arranged. The sealed chamber 201 has an inlet 205 for pressurized gas, for excerting a mechanical force on a membrane 203. The solenoid 202 normally operates on the membrane 203 by means of a push rod 204 and exerts a mechanical pressure determined by the current in the solenoid. During normal operation the sealed housing is vented to ambient environment, e.g. by means of a suitable valve, such that pneumatic operation of the membrane 203 in relation to expiratory pressure is minimally affected. When the solenoid is without current, the push rod is moved to the position shown in FIG. 5, out of contact with the membrane 203. A tube 206 is connected to the sealed chamber 201 at the inlet 205, and extends from a needle valve 207. The needle valve 207, or an equivalent pressure regulator, are of a commercially available type. Alternatively to tube 206 other solutions are provideable and comprise for instance a direct arrangement of the needle valve or pressure regulator on the wall interacting the sealed chamber 201.

The needle valve 207 controls the pressure in line 206 and thus inside the sealed chamber 201. The pressure inside the sealed chamber 201 influences upon the membrane 203, so that the expiratory valve 40 opens at a pressure determined by the internal pressure of the sealed chamber 201. The needle valve 207 may be controlled by a knob 208. A potentiometer/encoder 209 may be controlled by the same knob 208, so that the expiratory valve 40 is controlled to the same pressure as indicated and adjusted by the knob 208 during normal operation as well as during emergency operation. Thus, the expiratory valve 40 performs two operations, an electronically controlled, normal, operation and a mechanically controlled, emergency operation.

Figure 8:
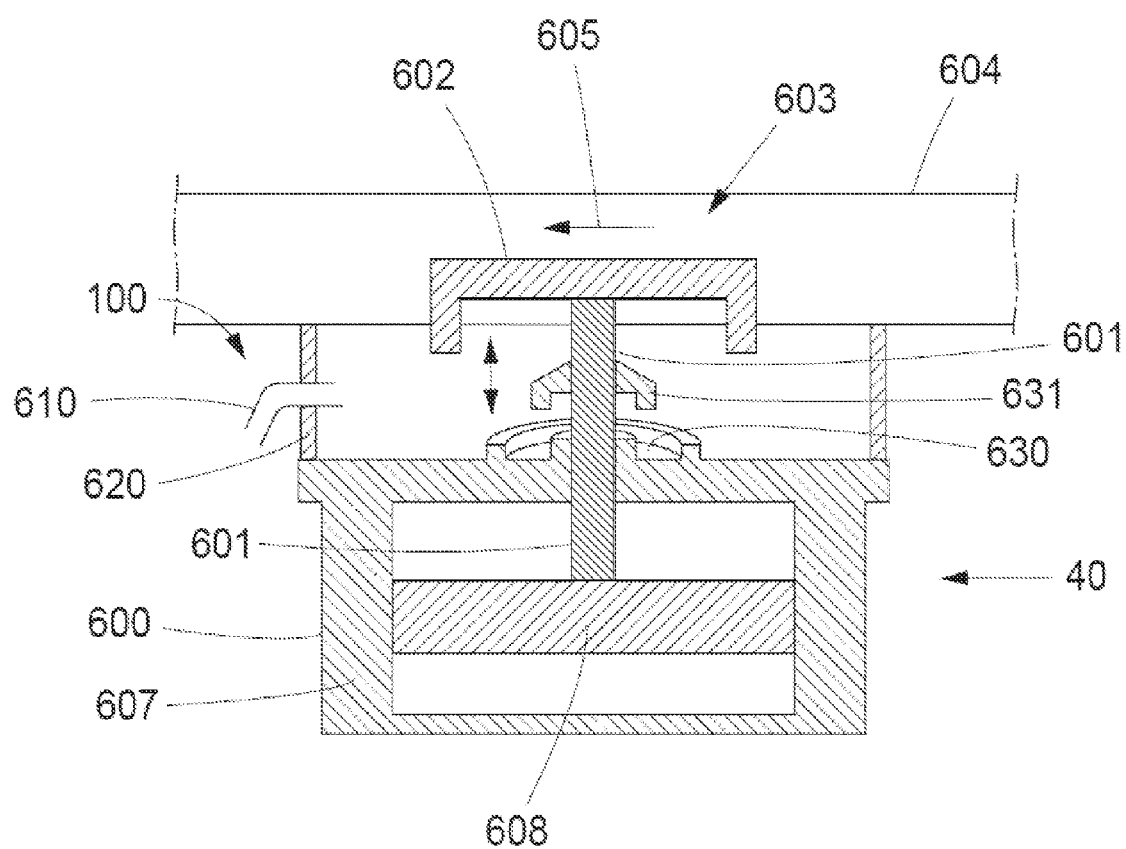
FIG. 8 is cross-sectional view of an expiratory valve according to a further embodiment.

FIG. 8 is cross-sectional view of an expiratory valve according to a further embodiment.

Like the embodiment shown in FIG. 6, the normally electrically operated expiratory valve 40 of the embodiment shown in FIG. 8 comprises a non-electrical expiratory valve backup control system 100. The expiratory valve 40 comprises a solenoid 600 driving a push rod 601 connected to an expiratory valve membrane 602. The solenoid may include, for instance, a permanent magnet 607 and a coil 608. An electrical current in coil 608 thus causes a relative movement of the coil and the push rod 601 in a longitudinal direction of the latter.

The expiratory valve membrane 602, when actuated upon by the push rod 601, changes a restriction 603 in an expiratory gas flow channel 604. Thus, an expiratory gas flow 605 and a pressure level in the expiratory gas flow channel 604 is controlled by the position of expiratory valve membrane 602 therein. In electrical operation of the anesthesia breathing apparatus, in which the expiratory valve 40 is installed, the solenoid is operated electrically in order to control the restriction 603.

During emergency manual ventilation the non-electrical expiratory valve backup control system 100 takes over control of restriction 603. In non-powered condition, the solenoid takes a position in the lower end thereof and the push rod 601 does no longer engage the lower side of the membrane 602. A pressure tight sealing is provided by a sealing 631 abutting against a sealing surface 630 provided on the housing of the solenoid 600. Thus, any pressure inside a housing 620 connecting the housing of the solenoid 600 is with the expiratory channel may not lead to leakage of into the housing of the solenoid.

The housing 620 is provided with a pneumatic input port 610 that is arranged to control the pressure inside the housing 620. The membrane 602 is arranged such that it is movable upon a pressure difference between a pressure in the expiratory channel 604 and a pressure in the interior of the housing 620. The membrane 602 is further arranged such that a leakage of gas between the expiratory channel 604 and the interior of the housing 620 is excluded. This may for instance be achieved by suitable sealing, a suitable resilient material of the membrane 602, or a thin continuous membrane of a mechanically strong material not hindering movement of the membrane relative the expiratory channel 604 and the interior of the housing 620. The housing 620 may be arranged releasably attachable to the expiratory channel. For instance the expiratory channel 604 may be arranged as a cassette that can be pushed against the upper part of the housing 620. In this way the inner of housing 620 will not get into contact with patient expiratory gases that might be biologically contaminated, and the expiratory valve is disinfectable between patients together with the remaining expiratory channel.

The position of the membrane 602 of in relation to the expiratory channel 604 is controllable by a pressure provided inside the housing 620. The membrane 602 moves further into the expiratory channel 604 upon increasing pressure inside the housing 620. Thus, the expiratory gas flow 605 and the expiratory pressure are controlled by the pressure inside housing 620. The pressure inside housing 620 is controllable via the pneumatic input 610. Thus, the operating pressure of the expiratory valve 40 may be non-electrically controlled by the pressure provided to the interior of housing 620, which in turn for instance is controlled by the adjustable pressure regulator 192, shown in FIG. 3 and FIG. 5.

This embodiment provides for a substantially maintenance free expiratory valve. The embodiment does not need to be cleaned or disinfected between patients, which often exposes valve material to wear and tear. Furthermore, no valve membranes of the backup part of the valve are present that regularly have to be exchanged during maintenance of the anesthesia breathing apparatus. The expiratory valve does not have to be disassembled during maintenance, which is contributing to low maintenance cost.

The present invention has been described above with reference to specific embodiments. However, other embodiments than the above described are equally possible within the scope of the invention. The different features of embodiments of the invention may be combined in other combinations than those described. The scope of the invention is only limited by the appended patent claims.

We claim:

1. A ventilatory valve that controls at least one of a expiratory flow or an expiratory pressure level in an expiratory branch of a patient breathing circuit of an anesthetic breathing apparatus, said ventilatory valve comprising:
    a valve unit having a controllable restriction that controls said expiratory flow and/or expiratory pressure in said patient breathing circuit;
    an electrical force transmission unit that electrically controls said restriction during electrical operation of said anesthetic breathing apparatus; and
    a pneumatic force transmission unit that pneumatically controls said restriction upon electrically defective or powerless operation of said anesthetic breathing apparatus
    wherein said controllable restriction comprises a membrane that is movably located in a gas flow channel of said expiratory branch.

2. The ventilatory valve according to claim 1, wherein said electrical force transmission unit is operative at during normal electrical operation of said anesthetic breathing apparatus and said pneumatic force transmission unit is operative during powerless emergency operation of said anesthetic breathing apparatus.

3. The ventilatory valve according to claim 1, wherein said ventilatory valve is an expiratory valve during a mechanical ventilation mode of said anesthetic breathing apparatus and an adjustable pressure limiting valve during a manual ventilation mode of said anesthetic breathing apparatus.

4. The ventilatory valve according to claim 1, wherein said electrical force transmission unit comprises a solenoid operated by an electric current for providing a mechanical force on said membrane, said mechanical force being adjustable by said electric current to adjust said restriction and thereby said expiratory flow and/or expiratory pressure.

5. The ventilatory valve according to claim 4, wherein said pneumatic force transmission unit comprises a mechanical unit that exerts said mechanical force on said membrane upon said electrically defective or powerless operation of said anesthetic breathing apparatus, said mechanical force being adjustable such that a limit of said expiratory pressure level is adjustable with said pneumatic force transmission unit.

6. The ventilatory valve according to claim 5, wherein said pneumatic force transmission unit comprises a sealed chamber controllably pressurized with a gas provided from a source of pressurized gas via an adjustable pressure regulator to exert said mechanical force on said membrane.

7. The ventilatory valve according to claim 6, wherein said solenoid is enclosed in said sealed chamber having an inlet for pressurized gas.

8. The ventilatory valve according to claim 6, wherein said solenoid comprises a solenoid housing to which said sealed chamber is attached and a push rod extending from said solenoid into said sealed chamber and wherein said push rod comprises a seal engaging a sealing surface of said solenoid housing in a powerless condition of said solenoid.

9. The ventilatory valve according to claim 5, wherein said mechanical unit comprises a push rod operated by said pneumatic unit.

10. The ventilatory valve according to claim 9, wherein said pneumatic force transmission unit transforms pressure into a defined mechanical movement when provided with a gas from a source of pressurized gas via an adjustable pressure regulator.

11. The ventilatory valve according to claim 10, wherein said pneumatic force transmission unit comprises a mushroom valve assembly.

12. The ventilatory valve according to claim 4, comprising a manual operating unit that adjusts said electric current in normal operation and said mechanical force in emergency operation.

13. An anesthetic breathing apparatus comprising:
    a patient breathing circuit having an expiratory branch having an expiratory flow and an expiratory pressure level therein;

a ventilatory valve that controls at least one of an expiratory flow or the expiratory pressure level in the expiratory branch of said patient breathing circuit, said ventilatory valve comprising a valve unit having a controllable restriction that controls said expiratory flow and/or expiratory pressure in said patient breathing circuit;

an electrical operating unit for said valve unit that electrically controls said restriction during electrical operation of said anesthetic breathing apparatus, and a non-electrical operating unit for said valve unit, that non-electrically controls said restriction upon electrical defective or powerless operation of said anesthetic breathing apparatus; and a manually operable emergency manual ventilation switch, which normally is in an off-position in which said anesthetic breathing apparatus in normal operation is supplied with electrical power, and is operational for at least one electrically controlled mechanical ventilation mode and a manual ventilation mode;

wherein said emergency manual ventilation switch comprises an on-position that causes said anesthetic breathing apparatus to be disconnected from said electrical power and to be operated in a pneumatically controlled manual ventilation operation mode and wherein said ventilatory valve, during said normal operation, is electrically controlled and, in said pneumatically controlled manual ventilation operation mode, is non-electrically controlled.

14. The anesthetic breathing apparatus according to claim 13, wherein said emergency manual ventilation switch is a combined electrical switch and pneumatic switch, in which a pneumatic line is interruptible and in which electric power supply to the anesthesia machine is controllable.

15. The anesthetic breathing apparatus according to claim 14, wherein when said emergency manual ventilation switch is in the on-position, the electric power to the anesthesia machine is interrupted and the pneumatic line is opened by said emergency manual ventilation switch, and wherein an adjustable metered amount of oxygen is supplied to the patient breathing circuit controllable by a manual ventilation bag.

16. The anesthetic breathing apparatus according to claim 13, wherein said emergency manual ventilation switch is automatically electrically operated, such that it enters the on-position upon a power failure.

17. A method of controlling a pressure level in a breathing circuit of an anesthetic breathing apparatus with a ventilatory valve in an expiratory branch of said anesthetic breathing apparatus, said method comprising the steps of:

electrically controlling an expiratory flow and/or expiratory pressure in said patient breathing circuit during electrical operation of said anesthetic breathing apparatus by a controllable restriction of said ventilatory valve; and manually controlling said expiratory flow and/or expiratory pressure in said patient breathing circuit of said anesthetic breathing apparatus by said controllable restriction of said ventilatory valve by manually controlling a pressure in a pneumatic circuit coupled to said ventilator valve during electrically defective or powerless operation of said anesthetic breathing apparatus.

* * * * *